(12) United States Patent
Cole et al.

(10) Patent No.: US 8,437,000 B2
(45) Date of Patent: May 7, 2013

(54) MULTIPLE WAVELENGTH CAVITY RING DOWN GAS SENSOR

(75) Inventors: Barrett E. Cole, Bloomington, MN (US); Terry Marta, White Bear Lake, MN (US); James Allen Cox, New Brighton, MN (US); Fouad Nusseibeh, Champlin, MN (US)

(73) Assignee: Honeywell International Inc., Morristown, NJ (US)

( * ) Notice: Subject to any disclaimer, the term of this patent is extended or adjusted under 35 U.S.C. 154(b) by 501 days.

(21) Appl. No.: 12/825,985

(22) Filed: Jun. 29, 2010

(65) Prior Publication Data
US 2011/0317164 A1    Dec. 29, 2011

(51) Int. Cl.
*G01N 21/00* (2006.01)

(52) U.S. Cl.
USPC .......................... 356/437; 356/436; 356/440

(58) Field of Classification Search .................. None
See application file for complete search history.

(56) References Cited

U.S. PATENT DOCUMENTS

| | | | |
|---|---|---|---|
| 4,051,372 A | 9/1977 | Aine | |
| 4,233,568 A | 11/1980 | Hamerdinger et al. | |
| 4,612,647 A | 9/1986 | Norvell | |
| 4,614,961 A | 9/1986 | Khan et al. | |
| 4,672,624 A | 6/1987 | Ford | |
| 4,732,480 A | 3/1988 | Fortunato et al. | |
| 4,795,258 A | 1/1989 | Martin | |
| 4,870,224 A | 9/1989 | Smith et al. | |
| 4,973,131 A | 11/1990 | Carnes | |
| 5,022,745 A | 6/1991 | Zayhowski et al. | |
| 5,040,895 A | 8/1991 | Laurent et al. | |

(Continued)

FOREIGN PATENT DOCUMENTS

| DE | 3311808 | 10/1984 |
|---|---|---|
| DE | 19635421 | 12/1997 |

(Continued)

OTHER PUBLICATIONS

Bernstein et al., "Development of a Miniature Silicon PhotoAcoustic Gas Sensor," Presented at Opto 96, Leipzig, Germany, 6 pages, Sep. 26-29, 1999.

(Continued)

*Primary Examiner* — L. G. Lauchman
*Assistant Examiner* — Juan D Valentin, II
(74) *Attorney, Agent, or Firm* — Seager Tufte & Wickhem LLC

(57) ABSTRACT

An illustrative cavity ring down gas sensor includes an optical cavity for receiving a gas to be detected and at least two electromagnetic radiation sources. The first electromagnetic radiation source may emit a first beam of light having a wavelength corresponding to an absorption wavelength of the gas to be detected, and the second electromagnetic radiation source may emit a second beam of light having a second wavelength that is off of an absorption wavelength of the gas to be detected. The first beam of light may detect a cavity ring down time decay, which is related to the concentration of the gas to be detected. The second beam of light may be used to detect a baseline cavity ring down time decay, which may be used to help increase the accuracy of the sensor by, for example, helping to compensate the concentration of the gas detected by the first beam of light for sensor variations caused by, for example, sensor age, temperature or pressure changes, and/or other conditions.

17 Claims, 4 Drawing Sheets

U.S. PATENT DOCUMENTS

| | | | |
|---|---|---|---|
| 5,135,304 A | 8/1992 | Miles et al. |
| 5,146,465 A | 9/1992 | Khan et al. |
| 5,278,435 A | 1/1994 | Van Hove et al. |
| 5,311,280 A | 5/1994 | Koper et al. |
| 5,408,319 A | 4/1995 | Halbout et al. |
| 5,418,868 A | 5/1995 | Cohen et al. |
| 5,450,053 A | 9/1995 | Wood |
| 5,468,910 A | 11/1995 | Knapp et al. |
| 5,512,750 A | 4/1996 | Yanka et al. |
| 5,528,040 A | 6/1996 | Lehmann |
| 5,544,186 A | 8/1996 | Sauer et al. |
| 5,550,373 A | 8/1996 | Cole et al. |
| 5,629,951 A | 5/1997 | Chang-Hasnain et al. |
| 5,677,538 A | 10/1997 | Moustakas et al. |
| 5,679,965 A | 10/1997 | Schetzina |
| 5,723,706 A | 3/1998 | Brasier et al. |
| 5,739,554 A | 4/1998 | Edmond et al. |
| 5,797,490 A | 8/1998 | Fujii et al. |
| 5,815,277 A | 9/1998 | Zare et al. |
| 5,832,017 A | 11/1998 | Ramdani et al. |
| 5,834,331 A | 11/1998 | Razeghi |
| 5,835,231 A | 11/1998 | Pipino |
| 5,847,397 A | 12/1998 | Moustakas |
| 5,869,896 A | 2/1999 | Baker et al. |
| 5,900,650 A | 5/1999 | Nitta |
| 5,909,280 A | 6/1999 | Zavracky |
| 5,912,740 A | 6/1999 | Zare et al. |
| 5,915,051 A | 6/1999 | Damask et al. |
| 5,933,245 A | 8/1999 | Wood et al. |
| 5,933,565 A | 8/1999 | Diebold |
| 5,960,025 A | 9/1999 | Thorland et al. |
| 5,982,788 A | 11/1999 | Hemmati |
| 6,040,895 A | 3/2000 | Haas |
| 6,080,988 A | 6/2000 | Ishizuya et al. |
| 6,084,682 A | 7/2000 | Zare et al. |
| 6,091,504 A | 7/2000 | Walker et al. |
| 6,115,122 A | 9/2000 | Bao et al. |
| 6,122,416 A | 9/2000 | Ooba et al. |
| 6,147,756 A | 11/2000 | Zavracky et al. |
| 6,208,798 B1 | 3/2001 | Morozov et al. |
| 6,233,052 B1 | 5/2001 | Zare et al. |
| 6,275,296 B1 | 8/2001 | Numai |
| 6,287,940 B1 | 9/2001 | Cole et al. |
| 6,295,130 B1 | 9/2001 | Sun et al. |
| 6,296,799 B1 | 10/2001 | Sato et al. |
| 6,310,904 B1 | 10/2001 | Thorland et al. |
| 6,324,192 B1 | 11/2001 | Tayebati |
| 6,335,669 B1 | 1/2002 | Miyazaki et al. |
| 6,377,350 B1 | 4/2002 | Paldus et al. |
| 6,380,531 B1 | 4/2002 | Sugihwo et al. |
| 6,384,953 B1 | 5/2002 | Russell et al. |
| 6,393,894 B1 | 5/2002 | Bonne et al. |
| 6,404,648 B1 | 6/2002 | Slupe et al. |
| 6,406,578 B1 | 6/2002 | Schober et al. |
| 6,421,127 B1 | 7/2002 | McAndrew et al. |
| 6,424,419 B1 | 7/2002 | Tazartes et al. |
| 6,438,149 B1 | 8/2002 | Tayebati et al. |
| 6,452,680 B1 | 9/2002 | Paldus et al. |
| 6,483,130 B1 | 11/2002 | Yang et al. |
| 6,483,149 B1 | 11/2002 | Mosher et al. |
| 6,490,034 B1 | 12/2002 | Woias et al. |
| 6,492,726 B1 | 12/2002 | Quek et al. |
| 6,507,107 B2 | 1/2003 | Vaiyapuri |
| 6,535,327 B1 | 3/2003 | Vodopyanov |
| 6,545,739 B1 | 4/2003 | Matsumoto et al. |
| 6,583,917 B2 | 6/2003 | Melloni et al. |
| 6,584,126 B2 | 6/2003 | Wang et al. |
| 6,590,710 B2 | 7/2003 | Hara et al. |
| 6,594,059 B2 | 7/2003 | Flanders |
| 6,597,713 B2 | 7/2003 | Ouchi |
| 6,608,711 B2 | 8/2003 | Flanders et al. |
| 6,627,983 B2 | 9/2003 | Tu et al. |
| 6,658,034 B2 | 12/2003 | Garnache et al. |
| 6,670,559 B2 | 12/2003 | Centola et al. |
| 6,670,599 B2 | 12/2003 | Wagner et al. |
| 6,728,286 B2 | 4/2004 | Thorland et al. |
| 6,741,381 B1 | 5/2004 | Levenson et al. |
| 6,784,946 B1 | 8/2004 | Schroter et al. |
| 6,792,010 B2 | 9/2004 | Koulikov et al. |
| 6,816,636 B2 | 11/2004 | Cole et al. |
| 6,836,501 B2 | 12/2004 | Cox et al. |
| 6,859,284 B2 | 2/2005 | Rella et al. |
| 6,865,198 B2 | 3/2005 | Taubman |
| 6,879,014 B2 | 4/2005 | Wagner et al. |
| 6,959,023 B1 | 10/2005 | Xie et al. |
| 6,959,024 B2 | 10/2005 | Paldus et al. |
| 6,967,976 B2 | 11/2005 | Xie et al. |
| 6,970,484 B2 | 11/2005 | Paldus et al. |
| 6,985,281 B2 | 1/2006 | Wagner et al. |
| 7,002,697 B2 | 2/2006 | Domash et al. |
| 7,012,696 B2 | 3/2006 | Orr et al. |
| 7,015,457 B2 | 3/2006 | Cole et al. |
| 7,035,298 B2 | 4/2006 | Vodopyanov et al. |
| 7,046,362 B2 | 5/2006 | Lehmann et al. |
| 7,049,004 B2 | 5/2006 | Domash et al. |
| 7,050,170 B2 | 5/2006 | Chilese et al. |
| 7,064,836 B2 | 6/2006 | Bechtel et al. |
| 7,089,781 B2 | 8/2006 | Petrovic et al. |
| 7,101,431 B2 | 9/2006 | Miner |
| 7,106,763 B2 | 9/2006 | Tan et al. |
| 7,113,256 B2 | 9/2006 | Butler et al. |
| 7,113,286 B2 | 9/2006 | Yan |
| 7,116,423 B2 | 10/2006 | Paldus et al. |
| 7,145,165 B2 | 12/2006 | Cox et al. |
| 7,147,165 B2 | 12/2006 | Mongin et al. |
| 7,147,695 B2 | 12/2006 | Mitra |
| 7,154,595 B2 | 12/2006 | Paldus et al. |
| 7,173,754 B2 | 2/2007 | Vodopyanov et al. |
| 7,221,827 B2 | 5/2007 | Domash et al. |
| 7,259,856 B2 | 8/2007 | Kachanov et al. |
| 7,263,871 B2 | 9/2007 | Selker et al. |
| 7,265,842 B2 | 9/2007 | Paldus et al. |
| 7,304,799 B2 | 12/2007 | Ma et al. |
| 7,352,464 B2 | 4/2008 | Chen et al. |
| 7,369,242 B2 | 5/2008 | Cole et al. |
| 7,420,686 B2 | 9/2008 | Tan |
| 7,535,573 B2 | 5/2009 | Kachanov et al. |
| 7,586,114 B2 | 9/2009 | Cole et al. |
| 7,612,885 B2 | 11/2009 | Cole et al. |
| 7,649,189 B2 | 1/2010 | Cole |
| 7,656,532 B2 | 2/2010 | Cole |
| 7,663,756 B2 | 2/2010 | Cole |
| 7,884,938 B2 * | 2/2011 | Cole .............................. 356/437 |
| 2002/0017452 A1 | 2/2002 | Zimmermann et al. |
| 2002/0191268 A1 | 12/2002 | Seeser et al. |
| 2004/0234198 A1 | 11/2004 | Wagner et al. |
| 2004/0255853 A1 | 12/2004 | Ma et al. |
| 2005/0030628 A1 | 2/2005 | Wagner et al. |
| 2005/0082480 A1 | 4/2005 | Wagner et al. |
| 2005/0105184 A1 | 5/2005 | Ma et al. |
| 2005/0254056 A1 | 11/2005 | Kachanov et al. |
| 2007/0133001 A1 | 6/2007 | Cox et al. |
| 2007/0146720 A1 | 6/2007 | Cox et al. |
| 2007/0195434 A1 | 8/2007 | Koulikov et al. |
| 2008/0137089 A1 | 6/2008 | Tan |
| 2008/0151248 A1 * | 6/2008 | Cole et al. ..................... 356/437 |
| 2009/0113988 A1 | 5/2009 | Koulikov |
| 2009/0185175 A1 | 7/2009 | Cole et al. |
| 2009/0323055 A1 | 12/2009 | Cole et al. |
| 2010/0027012 A1 | 2/2010 | Fritz et al. |

FOREIGN PATENT DOCUMENTS

| | | |
|---|---|---|
| EP | 0177918 | 3/1991 |
| EP | 0667548 | 8/1995 |
| EP | 1069658 | 1/2001 |
| EP | 1070943 | 1/2001 |
| EP | 1847825 | 10/2007 |
| EP | 1061618 | 11/2007 |
| JP | 03252172 | 11/1991 |
| JP | 05095130 | 4/1993 |
| JP | 7288334 | 10/1995 |
| KR | 1020060087792 | 8/2006 |
| WO | 9326049 | 12/1993 |
| WO | 9942875 | 8/1999 |
| WO | 2004068123 | 8/2004 |
| WO | 2006000120 | 1/2006 |

OTHER PUBLICATIONS

Brown, et al., "Visible-Blind UV Digital Camera Based on a 32*32 Array of GAN/AIGAN P-I-N Photodiodes," MRS Internet Journal of Nitride Semiconductor Research, vol. 451, pp. 1-10, Sep. 1999.

Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and Fabrication of 10×10 Micro-Spatial Light Modulator Array for Phase and Amplitude Modulation," Sensors and Actuators, vol. 78, No. 1, pp. 63-70, Jan. 1999.

Cole et al., "Microscopic Spectroscopy of Optical MEMS Devices," Topic 2 (Materials and Technology), Honeywell Laboratories, 2 pages, on or Around Dec. 11, 2000.

U.S. Appl. No. 12/826,095, filed Jun. 29, 2010.

Edwards, "Multiple-Traverse Absorption Cell Design," Journal of the Optical Society of America, vol. 51, No. 1, pp. 98-102, Jan. 1961.

Ferber et al., "A Miniature Silicon Photoacoustic Detector for Gas Monitoring Applications", presented at the MTEX International Conference on Sensors and Transducers, Birmingham, UK, 7 pages, Feb. 14, 2001.

Gillis et al., "Photoacoustic Spectroscopy for Quantitation of Trace Gases in Air," 2 pages, Chemical Science and Technology Laboratory National Institute of Standards and Technology, Industrial and Analytical Instruments and Services Forensics and Homeland Security, 2 pages, prior to Jul. 21, 2008.

He et al., "High-Resolution Cavity Ring-Down Absorption Spectroscopy of Nitrous Oxide and Chloroform Using a Near-Infrared CW Diode Laser," Chemical Physics Letters, vol. 289, pp. 527-534, Jun. 19, 1998.

Jerman et al., "A Miniature Fabry-Perot Interferometer with a Corrugated Silicon Diaphragm Support," Sensors and Actuators, vol. A29, No. 2, pp. 151-158, Nov. 1991.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser for Intracavity Saturated-Absorption Spectroscopy," Optical Spectroscopy, vol. 65, No. 2, pp. 265-267, 1988.

Manfredi et al., "JFET Preamplifiers for Low Noise Applications in Calorimetry and Radiation Spectroscopy," Nuclear Physics B (Proc. Suppl.) 44, pp. 613-616, 1995.

O'Keefe et al., "Cavity Ring-Down Optical Spectrometer for Absorption Measurements Using Pulsed Laser Sources," Review of Scientific Instruments, 59, 11 pages, 1988.

Paul et al., "Cavity Ringdown Measures Trace Concentrations," Laser Focus World, pp. 71-80, Mar. 1997.

Pipino et al., "Evanescent Wave Cavity Ring-Down Spectroscopy with a Total-Internal-Reflection Minicavity," Rev. Sci. Instrum., vol. 68, No. 8, pp. 2978-2989, Aug. 1997.

Raymond et al., "Use of a Monolithic Dual JFET in a Low Cost, Low Noise, Charge-Sensitive Preamplifier for Semiconductor Radiation Detectors," Phys. Med. Biol., vol. 33, No. 3, pp. 367-372, 1988.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239.

Sadeghi et al., "Cavity Ring Down Spectroscopy Applied to Plasma Diagnostics," Proc. Int. Symp. Laser-aided Plasma Diagnostics Lake Tahoe, CA, 8 pages, Sep. 1999.

Scherer et al., "Infrared Cavity Ringdown Laser Absorption Spectroscopy (IR-CRLAS) in Low Pressure Flames," Applied Physics B., vol. 64, pp. 699-705, 1997.

Schiwon et al., "Terahertz Cavity-Enhanced Attenuated Total Reflection Spectroscopy," Applied Physics Letters, vol. 86, 2005.

Schweber, "An Old Communications Problem Reoccurs in Optical-Communication-System Design—How it Works: Making the Laser Diode Tunable", EDN, 3 pages, Sep. 28, 2000.

Shimizu et al., "Stark Spectroscopy by 10µ Lasers Using a Multipath Cell," Journal of Applied Physics, vol. 46, No. 1, pp. 258-259, Jan. 1975.

Siegman, Lasers, Chapter 11-13, Copyright 1986.

Smirnov et al., "Dye Lasers Using a Three-Mirror Cavity with Lamp Excitation," 4 pages, 1981.

Spence et al., "A Laser-Locked Cavity Ring-Down Spectrometer Employing an Analog Detection Scheme," Review of Scientific Instruments, vol. 71, No. 2, pp. 347-353, Feb. 2000.

Sze, "Physics of Semiconductor Devices." pp. 763-765, John Wiley & Sons, N.Y., 1982.

Tayebati et al., "Microelectromechanical Tunable Filter with Stable Half Symmetric Cavity," Electronics Letters, IEE Stevanage, GB, vol. 34, No. 20, pp. 1967-1968, Oct. 1998.

Tayebati et. al., "Widely Tunable Fabry-Perot Filters Using High Index-Contrast DBRs," Design and Manufacturing of WDM Devices, Dallas, Texas, Nov. 4-5, 1997, SPIE vol. 3234, pp. 206-218, 1998.

Yang et al., "Back-Illuminated GAN/AIGAN Heterojunction Photodiodes With High Quantum Efficiency and Low Noise," Applied Physics Letters, vol. 73, No. 8, pp. 1086-1088, XP000777678, Aug. 24, 1998.

* cited by examiner

MULTIPLE WAVELENGTH CAVITY RING DOWN GAS SENSOR

FIELD

The present disclosure relates generally to gas sensors, and more particularly, to cavity ring down gas sensors.

BACKGROUND

Gas sensors are widely used across many diverse applications including commercial, industrial, military and other applications. The sensitivity of such gas sensors can vary, and the type of gas sensor used for a particular application is often selected depending on the required sensitivity and cost. In some applications, it may be desirable to detect gas concentrations as low as a few parts per billion, or even less. Many commercially available gas sensors do not have a high enough sensitivity or accuracy to detect these and other gas concentrations.

SUMMARY

The present disclosure relates generally to gas sensors, and more particularly, to cavity ring down gas sensors. In one illustrative embodiment, a gas sensor includes an optical cavity for receiving a gas to be detected, a first electromagnetic radiation source (e.g. laser), and a second electromagnetic radiation source (e.g. laser). The optical cavity is defined by one or more optical segments separating at least two mirrors. The first electromagnetic radiation source may be configured to emit a first beam of light having a first wavelength, wherein the first wavelength corresponds to an absorption line of a gas of interest. The second electromagnetic radiation source may be configured to emit a second beam of light having a second wavelength, where the second wavelength does not correspond to an absorption line of the gas of interest. The at least two mirrors can be configured to reflect the first beam of light and the second beam of light through the one or more optical segments, and thus the gas of interest. In some cases, the first beam of light and the second beam of light may be provided to the optical cavity simultaneously, while in other cases, the first beam of light and the second beam of light may be provided to the optical cavity sequentially, as desired.

A detector may be used to detect a first cavity ring down time decay of the first beam of light, which may be related to the absorption of the first beam of light by the gas of interest in the optical cavity, and thus may provide a measure that is related to the concentration of the gas of interest in the optical cavity. In some cases, the same detector may be used to detect a second cavity ring down time decay of the second beam of light in the optical cavity, which may correspond to a baseline cavity ring down time. In some cases, rather than using the same detector, a second detector may be used to detect a cavity ring down time decay of the second beam of light in the optical cavity. In either case, the baseline cavity ring down time may be used to help increase the accuracy of the sensor by, for example, helping to compensate for sensor variations such as sensor drift, which might be caused by, for example, sensor age, temperature or pressure changes, and/or other conditions.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION

The disclosure may be more completely understood in consideration of the following description of various illustrative embodiments of the disclosure in connection with the accompanying drawings, in which.

DESCRIPTION

Figure 1:
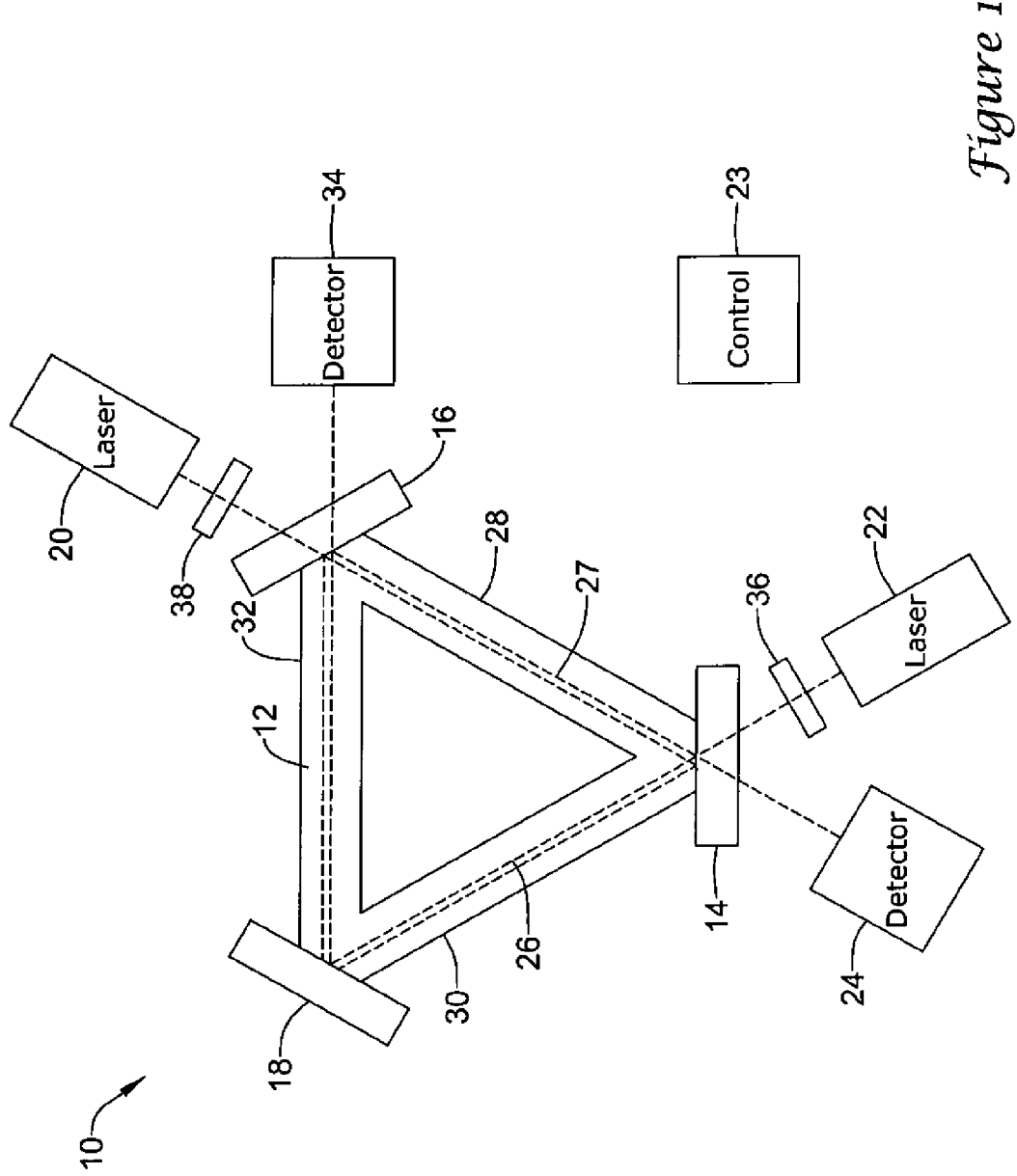
FIG. 1 is a schematic diagram of an illustrative multiple wavelength cavity ring down gas sensor.

The following description should be read with reference to the drawings wherein like reference numerals indicate like elements throughout the several views. The description and drawings show several examples of the claimed invention, and are not meant to be limiting in any way.

FIG. 1 is a schematic diagram of an illustrative multiple wavelength cavity ring down gas sensor 10. The illustrative multiple wavelength cavity ring down gas sensor 10 may provide a sensitive gas sensor that can be used to detect relatively low concentrations of gas in an environment. In some cases, the gas sensor 10 may be capable of accurately detecting gas concentrations as low as a few parts per billion, a few parts per trillion, or even a few parts per quadrillion, as desired.

In the illustrative embodiment of FIG. 1, multiple wavelength cavity ring down gas sensor 10 may include two or more electromagnetic radiation sources 20 and 22, such as lasers, an optical cavity 12 configured to receive a gas sample, and two or more detectors 24 and 34. The illustrative electromagnetic radiation sources 20 and 22, which in some cases may be lasers, light-emitting diodes (LEDs) or any other suitable light source, may each be configured to emit a beam of electromagnetic radiation, such as beams 26 and 27. In some embodiments, the beams 26 and 27 may be emitted by a coherent light source such as lasers 20 and 22. While not required, the lasers 20 and 22 may be tunable to different wavelengths, which may be useful to help identify a particular gas species in the gas sample. When so provided, light beam 26 of laser 22 may be tuned to a high (or other) absorption line, or wavelength close thereto, of a gas to be detected and light beam 27 of laser 20 may be tuned off of the high absorption line of the gas to be detected. In some cases, the lasers 20 and 22 may be infrared (IR) tunable input lasers that are tunable in or around the infrared band, but this is not required.

Alternatively, lasers 20 and 22 having fixed wavelengths (i.e. non-tunable) may be used. In this case, laser 22 may be selected to have a wavelength that is close to or at a high (or other) absorption line of a gas species to be detected, and laser 20 may be selected to have a wavelength that is off of the high absorption line of the gas species to be detected. In some cases, quantum cascade lasers may be suitable. Some example lasers include, for example, lasers available from New Focus™, such as the Velocity Product line, Telecom, or Daylight Solutions, such as a 4.5 micron laser model number TLS-21045, or a Chiller Model 1001 having a model number TLS-21045. These are only illustrative. When the lasers 20 and 22 have a fixed wavelength (i.e. non-tunable), the wavelength of the lasers to be used depends on the absorption spectra of the gas of interest. While lasers are used here as one example, this is not meant to be limiting in any way, and it is contemplated that any suitable electromagnetic radiation source may be used, as desired.

In the illustrative embodiment of FIG. 1, the optical cavity 12 has three linear optical segments 28, 30, and 32 arranged to define a triangular-shaped optical path of the optical cavity 12. In this illustrative embodiment, the optical cavity 12 includes three mirrors 14, 16, and 18 arranged so as to permit light beams 26 and 27 to travel in a continuous path around the optical cavity 12. As illustrated, mirrors 14, 16, and 18 are disposed in each of three corners of the optical cavity 12. As shown, mirror 14 intersects optical linear segment 28 and optical linear segment 30, mirror 16 intersects optical linear segment 30 and optical linear segment 32, and mirror 18 intersects optical linear segment 32 and optical linear segment 28 of optical cavity 12. While three mirrors are shown in the illustrative embodiment of FIG. 1, it is contemplated that more or less mirrors may be used, as desired. For example, it is contemplated that two mirrors that causes light beams to travel back and forth between the two mirrors can be used, or more than three mirrors may be used, as desired.

In the illustrative embodiment of FIG. 1, mirrors 14 and 16 may be passive mirrors, and mirror 18 may be an active mirror. In some cases, active mirror 18 may be deformable or otherwise actuatable, and passive mirrors 14 and 16 may be non-deformable. For example, passive mirrors 14 and 16 may be dielectric mirrors. In one illustrative embodiment, dielectric mirrors 14 and 16 may be configured to have a relatively high reflectivity on the internal surface and to be at least partially transparent on the external surface. The relatively high reflectivity on the internal surface of dielectric mirror 14 and 16 may help reflect light within the optical cavity 12 to reduce loss. The at least partial transparency on the external surface of, for example, mirror 14, may help incident light beam 26 pass through mirror 14 to enter the optical cavity 12.

In some cases, active mirror 18 may be mechanically and/or electrically deformable or otherwise actuatable so as to move the optical cavity 12 in and out of resonance conditions for the electromagnetic radiation sources 20 and 22. In the illustrative embodiment, the resonance condition for electromagnetic radiation source 22 may correspond to a wavelength for a high absorption line of the gas to be detected, while the resonance condition for electromagnetic radiation source 20 may correspond to a wavelength at which there is little or no absorption by the gas to be detected. In some cases, the active mirror 18 may be a piezoelectric mirror 18, but this is not required. When so provided, piezoelectric mirror 18 may be configured to deform when an electrical potential is applied across a piezoelectric element of the mirror 18. For example, an applied electrical potential may cause at least a portion of the mirror to expand and/or contract. In one example, the center of the piezoelectric mirror 18 may move in and out in response to the applied electrical potential, causing the position of the mirror 18 to change. In some embodiments, the electrical potential may oscillate, causing the piezoelectric mirror 18 to deform at a frequency of the applied oscillating electrical potential. The frequency that the active mirror 18 oscillates may dictate a chopping frequency at which light pulses are periodically applied to the optical cavity 12, with cavity ring down decay times in between.

In some cases, the piezoelectric mirror 18 may be configured to deform around one or more node positions. The one or more node positions may be positions of the piezoelectric mirror 18 in which the optical cavity 12 may have a resonance condition. For example, in one case, the piezoelectric mirror may have a first node position corresponding to the resonance condition for electromagnetic radiation source 22 and a second node position corresponding to the resonance condition for electromagnetic radiation source 20. When so provided, the oscillation of the piezoelectric mirror 18 may cause the optical cavity 12 to move in and out of the resonance conditions at the oscillating frequency of the piezoelectric mirror 18. In some cases, the resonance condition may occur twice for each oscillation cycle of the mirror 18, but could be more or less depending on the resonance conditions of the optical cavity 12. In one example, the oscillating frequency of the piezoelectric mirror 18 may be such that the resonance conditions of the optical cavity 12 occurs on the order of milliseconds, however, any suitable time period may be used. Similar to mirrors 14 and 16, piezoelectric mirror 18 may be configured to have a relatively high reflectivity on the internal surface to reduce loss, and in some cases, be at least partially transparent on the external surface, when desired.

In the illustrative embodiment shown in FIG. 1, passive mirrors 14 and 16 are entrance mirrors for the optical cavity 12, or more specifically, passive mirror 14 is the mirror in which the beam 26 passes through to enter the optical cavity 12, and passive mirror 16 is the mirror in which the beam 27 passes through to enter the optical cavity 12. It is contemplated, however, that both beam 26 and 27 may have the same entrance mirror, if desired. When the optical cavity 12 is in a resonance condition, the beam 26 or 27 that corresponds to the resonance condition that is coupled into the optical cavity 12 via passive mirror 14 or 16 may be amplified as the beam travels around and around the optical cavity 12 and as new light is added by the corresponding electromagnetic radiation sources 20 and 22. This amplification may help increasing the available sensitivity of the detection of gas in the optical cavity 12. In some cases, the amplification of the beams 26 and 27 may be on the order of 100 times to 1000 times or more relative to the amplitude of the light beam emitted by electromagnetic radiation sources 20 and 22. When the active mirror 18 causes the optical cavity 12 to fall out of resonance, the light beam traveling around the optical cavity 12 is stored for a period of time, typically on the order of microseconds, but decays with a cavity ring down time decay. The cavity ring down time decay will be dependent on the absorption of the light beams 26 or 27 by the gas that is present in the optical cavity 12, if any. In some cases, the active mirror 18 may cause the optical cavity 12 to fall out of resonance for one of the electromagnetic radiation sources (such as light source 20) and fall into resonance for the other one of the electromagnetic radiation sources (such as light source 22), and visa-versa.

Rather than (or in addition to) having an active mirror 18 that causes the optical cavity 12 to fall out of/into resonance to selectively control the initiation of a cavity ring down time decay time, in some embodiments, an acousto-optic (AO) modulator, such as AO modulators 36 and 38, can be associated with each of the electromagnetic radiations sources 20 and 22. The AO modulators 36 and 38 may be configured to selectively transmit the beams of light 26 and 27 into the optical cavity 12 and, in some cases, shut off the light that is input into the optical cavity 12 when the optical cavity 12 reaches a desired intensity. In some cases, the AO modulators 36 and 38 may receive a trigger signal from a detector (e.g. detectors 24, 34) that receives light leaking out of the optical cavity 12 through one of the mirrors. Rather than using AO modulators, it is contemplated that the electromagnetic radiations sources 20 and 22 themselves may be simply turned on and off by a controller, if desired.

Detectors 24 and 34 may be configured to detect the cavity ring down time decay of light beams 26 and 27 in the optical cavity 12. In some cases, the detectors 24 and 34 may be optical detectors that are configured to detect optical light that leaks out one of the mirrors, such as mirrors 14 and 16. In some cases, the detectors 24 and 34 may produce a zero measurement when no light is detected in the optical cavity 12.

In operation, the optical cavity 12 may couple in light beam 26 via mirror 14 and light beam 27 via mirror 16 at different times. In some cases, light beams 26 and 27 may be sequentially, alternatively, or otherwise coupled into optical cavity 12 at different times, as desired. This may be controlled by a control block 23. When the optical cavity 12 is in a resonance condition for light beam 26, e.g. according to the current state of the active mirror 18, the light beam 26 may be amplified and may interact with the gas sample in the optical cavity 12. In some cases, AO modulator 36 may shut off laser 22 when the intensity of the cavity reaches a desired level, as detected by Detector 24. Detector 24 may then detect a cavity ring down time decay of light beam 26, which is related to the absorption of the light beam 26 by the gas sample in the optical cavity 12.

When the optical cavity 12 is in a resonance condition for light beam 27, e.g. according to the current state of the active mirror 18, the light beam 27 is amplified, but since light beam 27 may not be at a high (or any other) absorption line of the gas to be detected, the light beam 27 may not significantly interact with the gas sample in the optical cavity 12. In some cases, AO modulator 38 may shut off laser 20 when the intensity of the cavity reaches a desired level, as detected by detector 34. Detector 34 may then detect a cavity ring down time decay of light beam 27, which may be used as a baseline cavity ring down time decay for the optical cavity 12. The baseline cavity ring down time decay can be used with the cavity ring down time decay of beam 26 to more accurately determine the concentration of the gas of interest in the optical cavity 12 by, for example, helping to compensate for sensor variations such as sensor drift, which might be caused by, for example, sensor age, temperature or pressure changes, and/or other conditions. Control block 23 may be coupled to detectors 24 and 34, and may use the baseline cavity ring down time decay to compensate a gas concentration value computed from the cavity ring down time decay of light beam 27. In some cases, the cavity ring-down time of the optical cavity may be on the order of micro-seconds, such as, for example, 10 micro-seconds, depending on the concentration and/or degree of absorption by the gas.

Figure 2:
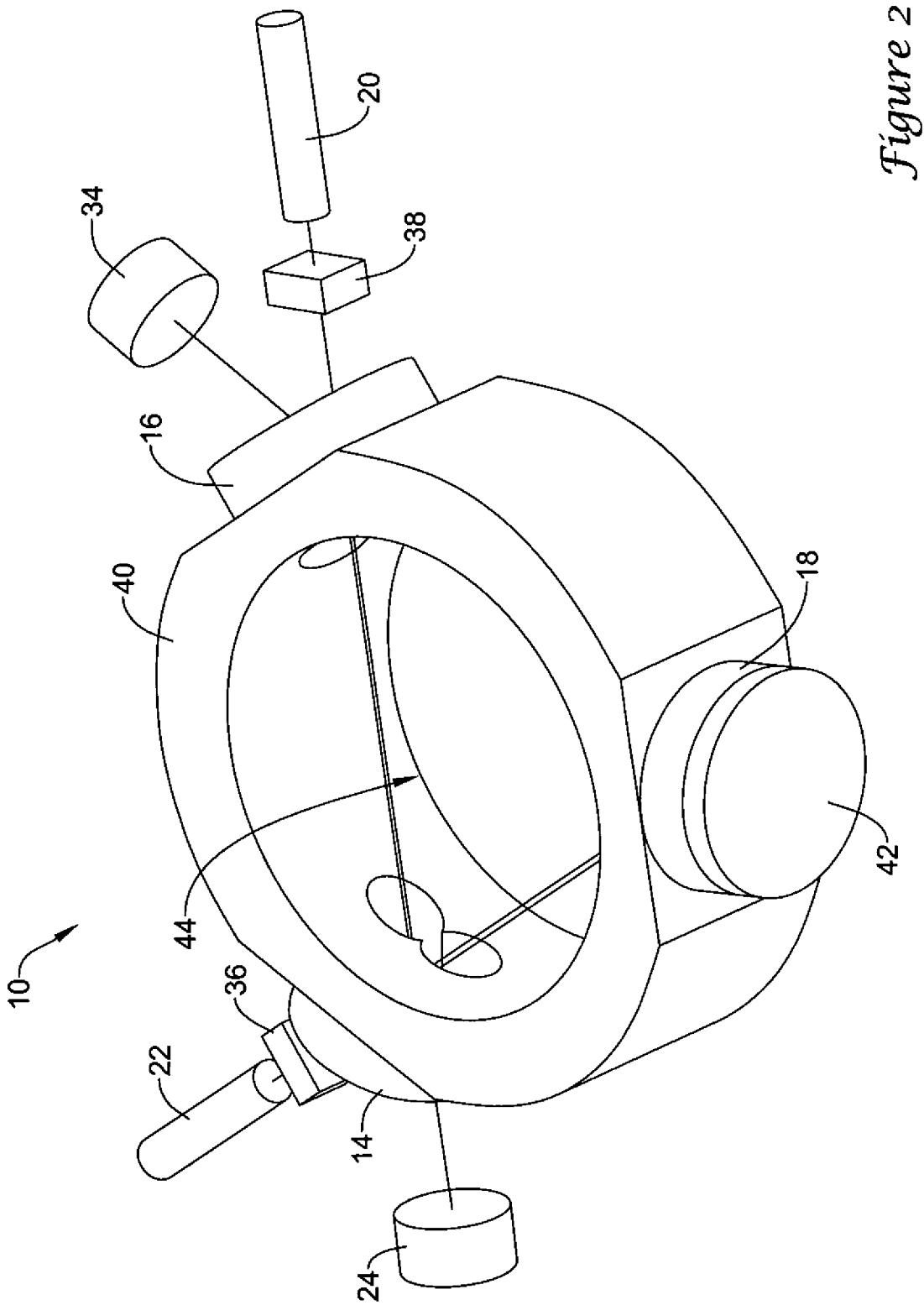
FIG. 2 is a perspective view of the illustrative multiple wavelength cavity ring down gas sensor of FIG. 1.

FIG. 2 is a perspective view of the illustrative multiple wavelength cavity ring down gas sensor 10 of FIG. 1. As illustrated, the optical cavity 12 is provided in a housing 40 defining optical segments 28, 30, and 32. As shown, the housing 40 may define a chamber 44 forming the optical cavity 12, while in other cases, it is contemplated that the housing 40 may include individual bores defining the individual segments 28, 30, and 32 of the optical cavity 12, if desired. The ends of optical segments 28, 30, and 32 may intersect mirrors 14, 16, and 18, which in the illustrative embodiment, are disposed about the side surfaces of the housing 40.

As shown, and in some illustrative embodiments, mirror 18 may include an actuator 42 for actuating the position of mirror 18. As noted above with respect to FIG. 1, mirror 18 may, in some cases, be an active mirror that may be mechanically and/or electrically deformable or otherwise actuatable so as to move the optical cavity in and out of resonance conditions for the electromagnetic radiation sources 20 and 22. In the illustrative embodiment, the resonance condition for electromagnetic radiation source 22 may correspond to a wavelength for a high absorption line of the gas to be detected, while the resonance condition for electromagnetic radiation source 20 may correspond to a wavelength at which there is little or no absorption by the gas to be detected. In some cases, the actuator 42 may be a piezoelectric actuator, but this is not required. When so provided, piezoelectric actuator 42 may be configured to deform the mirror 18 when an electrical potential is applied across a piezoelectric actuator. For example, an applied electrical potential may cause at least a portion of the mirror 18 to expand and/or contract. In one example, the center of the mirror 18 may move in and out in response to the applied electrical potential to the piezoelectric actuator, causing the position of the mirror 18 to change. In some embodiments, the electrical potential may oscillate, causing the piezoelectric actuator to deform at a frequency of the applied oscillating electrical potential. The frequency that the mirror 18 oscillates may dictate a chopping frequency at which light pulses are periodically applied to the optical cavity 12, with cavity ring down decay times in between.

In some cases, the piezoelectric actuator may cause mirror 18 to deform around one or more node positions. The one or more node positions may be positions of the mirror 18 in which the optical cavity 12 may have a resonance condition. For example, in one case, the mirror 18 may have a first node position corresponding to the resonance condition for electromagnetic radiation source 22, and a second node position corresponding to the resonance condition for electromagnetic radiation source 20. When so provided, the oscillation of the mirror 18 may cause the optical cavity 12 to move in and out of the resonance conditions at the oscillating frequency of the piezoelectric actuator. While a piezoelectric actuator is used as an example, it is contemplated that actuator 42 may be any suitable actuator, as desired.

Figure 3:
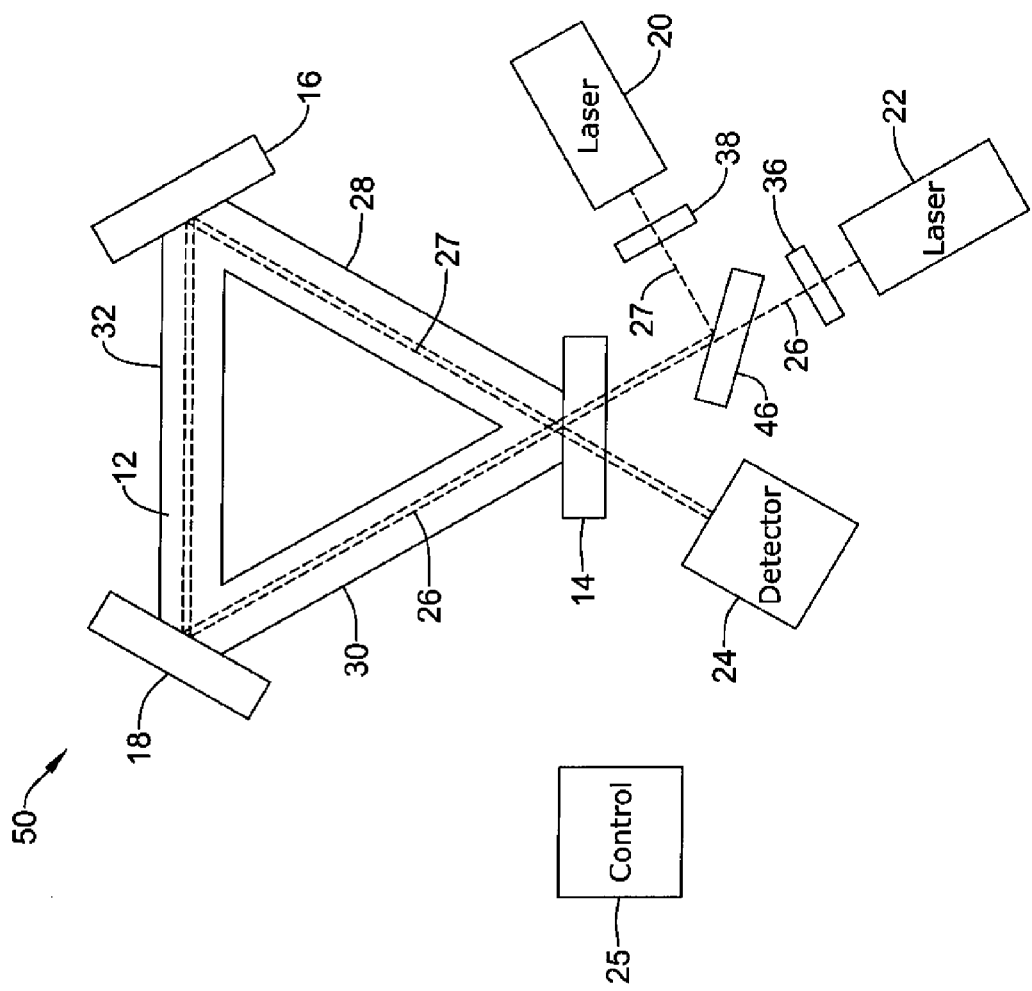
FIG. 3 is a schematic diagram of another illustrative multiple wavelength cavity ring down gas sensor.

FIG. 3 is a schematic diagram of another illustrative multiple wavelength cavity ring down gas sensor 50. In the illustrative embodiment, gas sensor 50 may be similar to gas sensor 10 shown in FIG. 1, except that light beams 26 and 27 enter the optical cavity 12 through a single entrance mirror, such as mirror 14, and, in some case cases, may include only a single detector, such as detector 24, for detecting the cavity ring down time decays of both light beams 26 and 27.

As shown in FIG. 3, a light coupling element 46 can be provided to direct both light beams 26 and 27 into the optical cavity 12. In some cases, light beams 26 and 27 may be directed into the optical cavity 12 sequentially, alternatively, or at non-simultaneous times, if desired. This may be controlled by a control block 25. For example, light beam 26 originating from laser 22 may pass through an AO modulator 36, light coupling element 46, and then the optical cavity 12 via mirror 14. Light beam 27 originating from laser 20 may, at a different time, pass through AO modulator 38 and be reflected or otherwise directed off of light coupling element 46 and enter optical cavity 12 via mirror 14. It is contemplated that light coupling element 46 may be a beam splitter, a fiber optic switching network, or any other suitable optical coupler that can direct the laser beams 26 and 27 into the optical cavity 12, as desired.

In the illustrative embodiment of FIG. 3, mirror 14 may be a passive mirror. In some cases, mirrors 16 and/or 18 may be active mirrors. In some cases, active mirrors 16 and/or 18 may be deformable or otherwise actuatable so as to move the optical cavity 12 in and out of the resonance conditions corresponding to the wavelengths of the electromagnetic radiation sources 20 and 22. In the illustrative embodiment, mirror 14 may be the only entrance mirror, but this is not required.

Detector 24 may be configured to detect the cavity ring down time decay of both light beams 26 and 27 in the optical cavity 12. In some cases, the detector 24 may be an optical detector that is configured to detect optical light that leaks out one of the mirrors, such as mirror 14. However, it is contemplated that separate detectors may be provided for light beams 26 and 27, if desired.

In operation, light beams 26 and 27 may be sequentially, alternatively, or otherwise coupled into optical cavity 12 at different times, as desired. When the optical cavity 12 is in a resonance condition for light beam 26, such as according to the current state of the active mirror 16 or 18, the light beam 26 is amplified and interacts with the gas sample in the optical cavity 12.

In some cases, AO modulator 36 may shut off laser 22 when the intensity of the cavity reaches a desired level. Detector 24 may then detect a cavity ring down time decay of light beam 26 that is related to the absorption of the light beam 26 by the gas sample.

When the optical cavity 12 is in a resonance condition for light beam 27, such as according to the current state of the active mirror 16 or 18, the light beam 27 is amplified, but since it is not at the high (or other) absorption line of the gas to be detected, it does not significantly interact with the gas sample in the optical cavity 12. In some cases, AO modulator 38 may shut off laser 20 when the intensity of the cavity reaches a desired level. Detector 24 then may detect a cavity ring down time decay of light beam 27. As discussed above, the cavity ring down time decay of light beam 27 may be used as a baseline cavity ring down time decay of the optical cavity 12. The baseline cavity ring down time decay can be used with the cavity ring down time decay of beam 26 to more accurately determine the concentration of the gas of interest in the optical cavity 12 by, for example, helping to compensate for sensor variations such as sensor drift, which might be caused by, for example, sensor age, temperature or pressure changes, and/or other conditions. Control block 25 may be coupled to detector 24, and may use the baseline cavity ring down time decay to compensate a gas concentration value computed from the cavity ring down time decay of light beam 27. In some cases, the cavity ring-down time of the optical cavity may be on the order of micro-seconds, such as, for example, 10 micro-seconds, depending on the concentration and/or degree of absorption by the gas.

Figure 4:
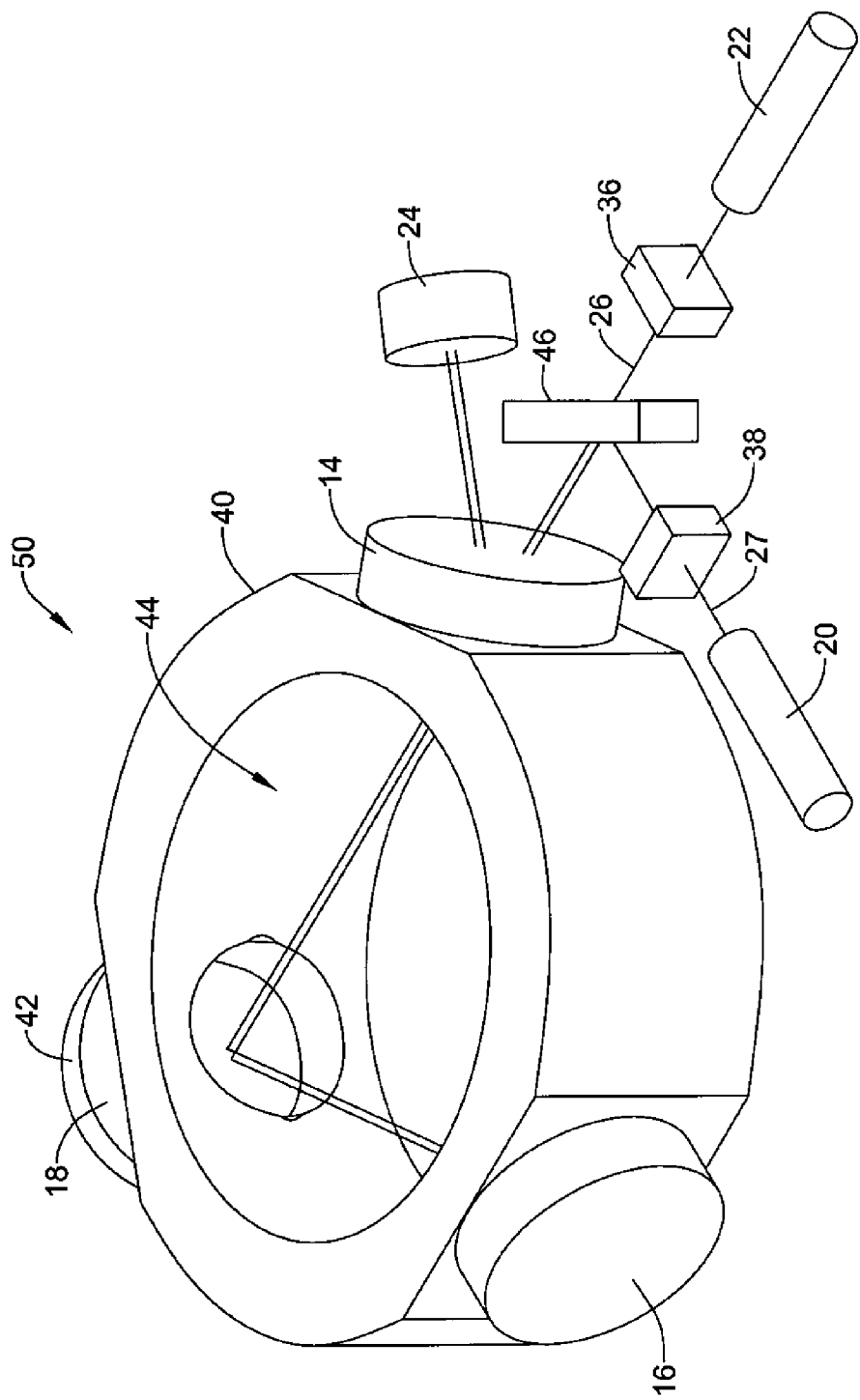
FIG. 4 is a perspective view of the illustrative multiple wavelength cavity ring down gas sensor of FIG. 3.

FIG. 4 is a perspective view of the illustrative multiple wavelength cavity ring down gas sensor 50 of FIG. 3. As illustrated, the optical cavity 12 is provided in housing 40 defining the optical segments 28, 30, and 32. As shown, the housing 40 may define a chamber 44, while in other cases, it is contemplated that the housing 40 may define individual optical segments 28, 30, and 32, if desired. The ends of optical segments 28, 30, and 32 may intersect mirrors 14, 16, and 18, which in the illustrative embodiment, are disposed about the side surfaces of the housing 40. As shown, and in some cases, mirror 18 may include actuator 42 for actuating the position of mirror 18, as further described above.

It should be understood that the above-described optical cavity 12 is only illustrative, and that the optical cavity 12 can take on any form that permits incoming light beams 26 and 27 to be introduced into the cavity 12, travel around and be amplified by the cavity 12, and allow direct or indirect measurement of the cavity ring down time decays of light beams 26 and 27 in the optical cavity 12.

Having thus described some illustrative embodiments of the present disclosure, those of skill in the art will readily appreciate that yet other embodiments may be made and used within the scope of the claims hereto attached. It will be understood that this disclosure is, in many respect, only illustrative. Changes may be made in details, particularly in matters of shape, size, and arrangement of parts without exceeding the scope of the disclosure. The invention's scope is, of course, defined in the language in which the appended claims are expressed.

What is claimed is:

1. A gas sensor for detecting a gas of interest, the gas of interest having one or more absorption lines, the gas sensor comprising:
   an optical cavity for receiving the gas of interest, the optical cavity defined by one or more optical segments separating at least two mirrors;
   a first electromagnetic radiation source configured to emit a first beam of light having a first wavelength, wherein the first wavelength corresponds to one of the one or more absorption lines of the gas of interest;
   a second electromagnetic radiation source configured to emit a second beam of light having a second wavelength, wherein the second wavelength does not correspond to any of the one or more absorption lines of the gas of interest;
   wherein the at least two mirrors are configured to reflect the first beam of light and the second beam of light through the one or more optical segments of the optical cavity and the gas of interest; and
   a first detector configured to detect a cavity ring down time decay of the first beam of light corresponding to an absorption of the first beam of light by the gas in the optical cavity;
   wherein at least one of the at least two mirrors is actuatable to move the optical cavity in and out of one or more node positions that provide one or more resonance conditions in the optical cavity; and
   wherein at least one of the at least two mirrors that is actuatable is electrically deformable, wherein the electrically deformable mirror deforms around the one or more node positions according to an applied electrical potential.

2. The gas sensor of claim 1, wherein the first detector is also configured to detect a cavity ring down time decay of the second beam of light in the optical cavity, indicating a baseline cavity ring down time.

3. The gas sensor of claim 1, further comprising a second detector configured to detect a cavity ring down time decay of the second beam of light in the optical cavity, indicating a baseline cavity ring down time.

4. The gas sensor of claim 1 wherein the electrically deformable mirror is a piezoelectric mirror.

5. The gas sensor of claim 1 further comprising an optical element that directs both the first beam of light and the second beam of light into the optical cavity.

6. The gas sensor of claim 1 wherein a first mirror of the at least two mirrors is an entrance mirror configured to couple both at least a portion of the first beam of light from the first electromagnetic radiation source and at least a portion of the second beam of light from the second electromagnetic radiation source into the optical cavity.

7. The gas sensor of claim 1 wherein a first mirror of the at least two mirrors is a first entrance mirror configured to couple at least a portion of the first beam of light from the first electromagnetic radiation source into the optical cavity, and a second mirror of the at least two mirrors is a second entrance mirror configured to couple at least a portion of the second beam of light from the second electromagnetic radiation source into the optical cavity.

8. The gas sensor of claim 1 wherein the first beam of light and the second beam of light are sequentially coupled into the optical cavity.

9. A gas sensor comprising:
a first laser configured to emit a first beam of light having a first wavelength that corresponds to an absorption wavelength of a gas to be detected;
a second laser configured to emit a second beam of light having a second wavelength that is different than the first wavelength;
an optical cavity including at least two mirrors separated by one or more optical segments, wherein the at least two mirrors couple the first beam of light from the first laser and the second beam of light from the second laser into the optical cavity, wherein at least one of the at least two mirrors is electrically tunable to move the optical cavity in and out of two or more resonance conditions, wherein a first resonance condition corresponds to the first wavelength, and a second resonance condition corresponds to the second wavelength, and wherein the one or more of the at least two mirrors that is electrically tunable is configured to deform the mirror around at least one node position according to an applied electrical signal; and
one or more optical detectors for detecting a first cavity ring down time decay of the first beam of light in the optical cavity, and a second cavity ring down time decay of the second beam of light in the optical cavity.

10. The gas sensor of claim 9 wherein the first beam of light and the second beam of light are sequentially coupled into the optical cavity according to the position of the at least one tunable mirror.

11. The gas sensor of claim 9 wherein the first beam of light is coupled into the optical cavity via a first mirror and the second beam of light is coupled into the optical cavity via a second mirror.

12. The gas sensor of claim 9 wherein the first beam of light and the second beam of light are coupled into the optical cavity via a common optical element.

13. A method of detecting a gas, the method comprising:
providing an optical cavity including at least two mirrors separated by one or more optical segments, wherein the optical cavity is configured to receive a gas;
coupling a first light beam having a first wavelength from a first electromagnetic radiation source into the optical cavity, wherein the first wavelength corresponds to an absorption wavelength of the gas in the optical cavity;
electrically deforming at least one of the at least two mirrors to move the optical cavity into a resonance condition at the first wavelength;
detecting a first cavity ring down time decay of the first beam of light in the optical cavity;
coupling a second light beam having a second wavelength from a second electromagnetic radiation source into the optical cavity, wherein the second wavelength corresponds to a wavelength that has relatively little or no absorption by the gas in the optical cavity;
electrically deforming at least one of the at least two mirrors to move the optical cavity into a resonance condition at the second wavelength; and
detecting a second cavity ring down time decay of the second beam of light in the optical cavity, indicating a baseline cavity ring down time.

14. The method of claim 13, wherein the first light beam is coupled into the optical cavity by tuning a first mirror of the optical cavity to a first node position.

15. The method of claim 14, wherein the second light beam is coupled into the optical cavity by tuning the first mirror of the optical cavity to a second node position.

16. The method of claim 13, wherein a first mirror of the at least two mirrors is an entrance mirror for the first beam of light and the second beam of light.

17. The method of claim 13, wherein a first mirror of the at least two mirrors is an entrance mirror for the first beam of light and a second mirror of the at least two mirrors is an entrance mirror for the second beam of light.

* * * * *